(12) United States Patent
Yi et al.

(10) Patent No.: US 12,725,704 B2
(45) Date of Patent: Sep. 1, 2026

(54) CIRCUIT PROVIDING ARTIFICIAL TACTILE NEURON AND APPARATUS FOR PREDICTING DISEASE BASED ON THE SAME

(71) Applicant: KOREA INSTITUTE OF SCIENCE AND TECHNOLOGY, Seoul (KR)

(72) Inventors: Hyunjung Yi, Seoul (KR); Suyoun Lee, Seoul (KR); Junseok Lee, Seoul (KR); Seon Jeong Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 1051 days.

(21) Appl. No.: 17/889,483

(22) Filed: Aug. 17, 2022

(65) Prior Publication Data

US 2023/0206047 A1 Jun. 29, 2023

(30) Foreign Application Priority Data

Dec. 24, 2021 (KR) ........................ 10-2021-0186753

(51) Int. Cl.
*G16H 50/20* (2018.01)
*G01L 1/18* (2006.01)

(52) U.S. Cl.
CPC ............... *G16H 50/20* (2018.01); *G01L 1/18* (2013.01)

(58) Field of Classification Search
None
See application file for complete search history.

(56) References Cited

U.S. PATENT DOCUMENTS 11,188,816 B2 11/2021 Kim et al.
11,464,589 B1 * 10/2022 Roh ........................ G16H 40/20
2017/0236027 A1 8/2017 van der Made et al.
2017/0236051 A1 8/2017 van der Made et al.
2021/0372261 A1 * 12/2021 Miller ................ G05B 13/0265

FOREIGN PATENT DOCUMENTS

JP 2021-140320 A 9/2021
KR 10-2018-0103375 A 9/2018

OTHER PUBLICATIONS

Tee, Benjamin C-K., et al. "A skin-inspired organic digital echanoreceptor." *Science* vol. 350 Issue 6258 (Jul. 5, 2015): pp. 313-316.

(Continued)

*Primary Examiner* — Farhana A Hoque
(74) *Attorney, Agent, or Firm* — NSIP Law

(57) ABSTRACT

Disclosed are a circuit for providing an artificial tactile neuron, and an apparatus for predicting a disease based on the circuit for providing an artificial tactile neuron. The circuit for providing an artificial tactile neuron according to an embodiment includes a piezoresistive device that receives pressure applied from an external object and changes a magnitude of resistance based on the pressure; and a switching device that changes a magnitude of resistance based on a voltage applied from an input voltage, wherein the pressure and a mechanical property of the external object are quantified from an output voltage set based on the input voltage and the voltage applied to the switching device.

16 Claims, 13 Drawing Sheets

(56) References Cited

OTHER PUBLICATIONS

Wan, Changjin, et al. "An artificial sensory neuron with tactile perceptual learning." *Advanced Materials* vol. 30.30 (Jun. 7, 2018): 1801291.
Wan, Haochuan, et al. "Flexible carbon nanotube synaptic transistor for neurological electronic skin applications." *ACS nano* 14.8 (Jul. 17, 2020): pp. 10402-10412.
Lee, Kyuho, et al. "Artificially intelligent tactile ferroelectric skin." *Advanced Science* vol. 7.22 (Sep. 3, 2020): 2001662.
Kim, Yeongin, et al. "A bioinspired flexible organic artificial afferent nerve." *Science* vol. 360.6392 (Jun. 1, 2018): pp. 998-1003.
Korean Office Action issued on Sep. 22, 2025 in corresponding Korean Patent Application No. 10-2021-0186753. (1 page in English and 1 page in Korean).

* cited by examiner

CIRCUIT PROVIDING ARTIFICIAL TACTILE NEURON AND APPARATUS FOR PREDICTING DISEASE BASED ON THE SAME

DESCRIPTION OF GOVERNMENT-SPONSORED RESEARCH

This research was carried out with the support of Personal Basic Research (Ministry of Science and ICT) (R&D) of the Ministry of Science and ICT [Development of multifunctional spiking tactile sensory neuron devices with spatiotemporal resolution, project identification number: 1711130022, detailed project number: NRF-2021R1A2C3011450].

CROSS-REFERENCE TO RELATED APPLICATION

The present application claims priority to Korean Patent Application No. 10-2021-0186753, filed Dec. 24, 2021, the entire contents of which are incorporated herein for all purposes by this reference.

BACKGROUND OF THE INVENTION

Field of the Invention

Disclosed embodiments relate to a circuit for providing an artificial tactile neuron and an apparatus for predicting a disease based on the same.

Description of the Related Art

The mechanical property of a biological system provides useful information about its biochemical state. For example, from the stiffness distribution of a tissue, a solid tumor can be easily identified from surrounding normal tissue. Therefore, identifying the mechanical property of a biological system can be a useful indicator in diagnosing a disease or determining the status of a lesion.

However, in order to analyze the mechanical property of a biological system in a conventional way, the opinion of an expert in the related field and a data-intensive computing process are essential. Nevertheless, the computing process presents several problems in terms of efficiency and energy consumption, and expert opinions cannot necessarily be guaranteed. Considering this, the analysis by the conventional method may be limited.

However, this limitation can be addressed by artificially mimicking the information processing method used by biological sensory neurons. Specifically, when a biological sensory neuron receives an external stimulus, it generates a corresponding spike signal and transmits it to the brain, which is a biological central processor. Here, the method for generating spike patterns by the biological sensory neuron plays a key role in reducing the burden of energy and information processing.

In this regard, some have reported several pioneering works on artificial mechanoreceptors, artificial afferent nerves, and tactile skin, but there are limitations in that the structure is complex or the mechanical property in small units cannot be identified. Therefore, there is a need to develop an artificial tactile neuron that can completely mimic a processing method of biological sensory neuron information with a simple structure.

SUMMARY OF THE INVENTION

Disclosed embodiments are to provide a circuit for providing an artificial tactile neuron and an apparatus for predicting a disease based on the same.

A circuit for providing an artificial tactile neuron according to an embodiment includes a piezoresistive device that receives pressure applied from an external object and changes a magnitude of resistance based on the pressure; and a switching device that changes a magnitude of resistance based on a voltage applied from an input voltage, wherein the pressure and a mechanical property of the external object are quantified from an output voltage set based on the input voltage and the voltage applied to the switching device.

The pressure may be quantified based on a frequency of a spike pattern of the output voltage, and the mechanical property of the external object may be quantified based on a change rate per unit time of the frequency of the spike pattern.

The mechanical property may include one or more of stiffness and hardness of the external object.

The voltage applied to the switching device is applied based on a voltage divider rule between the switching device and the piezoresistive device.

The switching device may be in a switched-off state when no voltage is applied, perform a switched-on when the applied voltage reaches a threshold voltage or higher, perform the switched-off when the applied voltage reaches a holding voltage or less in the switched-on state, and perform the switched-on when the applied voltage again reaches the threshold voltage or higher.

The magnitude of resistance of the switching device may be changed to an off-resistance value in the switched-off state, and an on-resistance value smaller than the off-resistance value in the switched-on state.

The switching device may perform the switch-on when the applied voltage reaches the threshold voltage as the pressure applied to the piezoresistive device increases and the magnitude of resistance of the piezoresistive device decreases.

The switching device may perform the switch-off when the applied voltage reaches the holding voltage as the pressure applied to the piezoresistive device is removed and the magnitude of resistance of the piezoresistive device increases.

The switching device may perform the switch-off when the applied voltage reaches the holding voltage as the magnitude of resistance of the switching device decreases to the on-resistance value in the switched-on state.

The switching device may again perform the switch-on when the applied voltage reaches the threshold voltage as the magnitude of resistance of the switching device increases to the off-resistance value in the switched-off state.

In the switching device, the magnitude of resistance of the switching device may be changed to the on-resistance value when the magnitude of the applied voltage reaches the threshold voltage as the pressure applied to the piezoresistive device increases and the magnitude of resistance of the piezoresistive device decreases.

The magnitude of resistance of the switching device may be changed to the off-resistance value when the magnitude of the applied voltage reaches the holding voltage as the pressure applied to the piezoresistive device is removed and the magnitude of resistance of the piezoresistive device increases.

The switching device may be connected in series with the piezoresistive device, and the circuit may further include a capacitor connected in parallel with the serially connected switching device and piezoresistive device.

An apparatus for predicting a disease based on an artificial tactile neuron according to an embodiment includes a circuit for providing an artificial tactile neuron including a piezoresistive device that receives pressure applied to a diagnosis target and changes a magnitude of resistance based on the pressure, and a switching device that changes a magnitude of resistance based on a voltage applied from an input voltage, wherein the pressure and a mechanical property of the diagnosis target are quantified from an output voltage set based on the input voltage and the voltage applied to the switching device; and a predictor that predicts a disease of the diagnosis target by inputting input data generated based on a quantified value for each of the pressure and the mechanical property into a pre-trained model.

The disclosed embodiments can mimic a tactile neuron using only the switching device and the piezoresistive device, so that an artificial tactile neuron can be provided with a simple configuration.

The disclosed embodiments can quantify the mechanical property of a biological system even with the pressure in a small unit, and thus provide a highly sensitive artificial tactile neuron.

The disclosed embodiments may predict a disease of a diagnosis target through change distribution of the pressure applied from a diagnosis target, and thus the stiffness distribution of a diagnosis target.

DETAILED DESCRIPTION OF THE INVENTION

Figure 1:
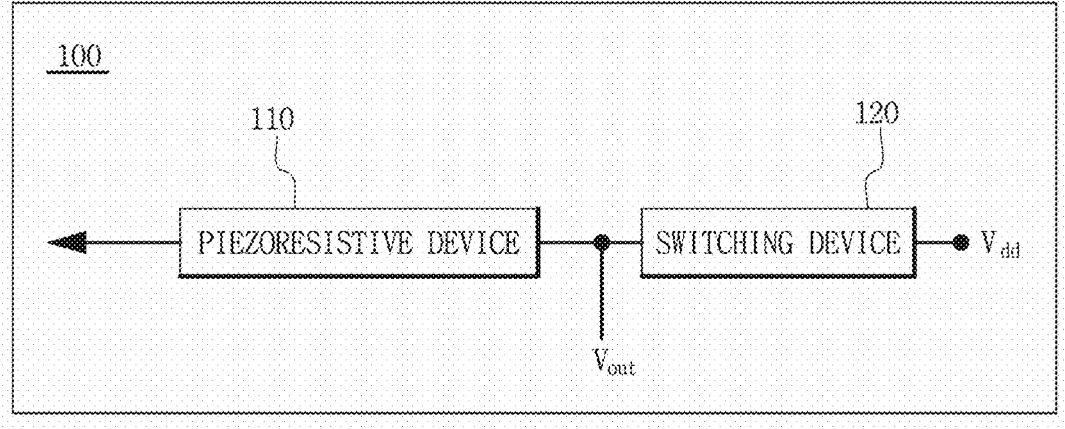
FIG. 1 is a circuit diagram illustrating a circuit for providing an artificial tactile neuron according to an embodiment.

Reference is made to the accompanying drawings, which show by way of illustration specific embodiments in which the present invention may be practiced. These embodiments are described in sufficient detail to enable those skilled in the art to practice the present invention. It should be understood that the various embodiments herein are different but need not be mutually exclusive. For example, certain shapes, structures, and characteristics in one embodiment described herein may be embodied in another embodiment without departing from the spirit and scope of the specification. In addition, it should be understood that the location or arrangement of individual components within each disclosed embodiment may be changed without departing from the spirit and scope of the present specification. Accordingly, the following detailed description is not intended to be taken in a limiting sense, and the scope of the present specification is limited only by the appended claims, along with all equivalents as claimed by the claims. Like reference numerals in the drawings refer to the same or similar functions throughout the various aspects.

The terms used in the present specification have been selected as widely used general terms as possible while considering their functions, but may vary depending on the intention or custom of a person skilled in the art or the advent of new technology. In addition, in a specific case, there are also terms arbitrarily selected by the applicant, and in this case, the meaning will be described in the description of the corresponding specification. Therefore, it is intended to clarify that the terms used in this specification should be interpreted based on the actual meaning of the terms and the contents of the entire specification, rather than the simple names of terms.

Further, embodiments described herein may have aspects that are entirely hardware, partially hardware, and partially software, or entirely software. In this specification, "unit", "module", "device", "server" or "system" etc. Refers to a computer-related entity such as hardware, a combination of hardware and software, or software. For example, a part, module, device, server, or system may refer to hardware constituting a part or all of a platform and/or software such as an application for driving the hardware.

Hereinafter, an embodiment will be described in detail with reference to the accompanying drawings and the contents described in the accompanying drawings, but the scope of the claims is not limited or limited by the embodiments.

FIG. 1 is a circuit diagram illustrating a circuit 100 for providing an artificial tactile neuron according to an embodiment.

Referring to FIG. 1, a circuit 100 for providing an artificial tactile neuron includes a piezoresistive device 110 and a switching device 120.

The piezoresistive device 110 receives the pressure applied from an external object, and changes a magnitude of resistance based on the pressure.

Here, the external object may include various biological systems. The external object may include various levels of biological systems, such as organs, tissues, and cells of an organism. As a specific example, the external object may include a part of a body organ including a tumor.

According to an embodiment, the piezoresistive device 110 may receive a direct pressure applied from the external object applying a force or an indirect pressure applied from an external force pressing the external object.

According to an embodiment, the piezoresistive device 110 may be a device in which the magnitude of electrical resistance changes as the pressure applied from the external object changes. For example, the piezoresistive device 110 may be a piezoresistive sensor (PRS) in which the magnitude of electrical resistance of the device is changed according to the applied pressure.

That is, the piezoresistive device 110 may sense a degree of applied pressure through the changed magnitude of electrical resistance. Accordingly, the piezoresistive device 110 may replace the function of a mechanoreceptor of a sensory neuron that senses the pressure applied from the external object.

Meanwhile, in the present specification, the piezoresistive device 110 has been illustrated and described as a configuration corresponding to the mechanoreceptor of the sensory neuron, but this is not necessarily limited thereto, and other devices whose property may change with pressure may be included.

The magnitude of resistance of the switching device 120 is changed based on the voltage applied to the switching device from an input voltage (Vdd).

According to an embodiment, the switching device 120 may reversibly perform a switch-off when the applied voltage reaches less than or equal to a holding voltage, and a switch-on when the applied voltage reaches a threshold voltage or more.

For example, the switching device 120 may perform the switch-on when the voltage applied to the switching device 120 reaches the threshold voltage as the pressure applied to the piezoresistive device 110 increases and the magnitude of resistance of the piezoresistive device 110 decreases.

As another example, the switching device 120 may perform the switch-off when the voltage applied to the switching device 120 reaches the holding voltage as the pressure applied to the piezoresistive device 110 is removed and the magnitude of resistance of the piezoresistive device 110 increases.

According to an embodiment, the magnitude of resistance of the switching device 120 may be changed to an off-resistance value in a switched-off state, and an on-resistance value in a switched-on state.

For example, the magnitude of resistance of the switching device 120 may be changed to an on-resistance value when the magnitude of voltage applied to the switching device 120 reaches the threshold voltage as the pressure applied to the piezoresistive device 110 increases and the magnitude of resistance of the piezoresistive device 110 decreases.

As another example, the magnitude of resistance of the switching device 120 may be changed to an off-resistance value when the magnitude of the voltage applied to the switching device 120 reaches the holding voltage as the pressure applied to the piezoresistive device 110 is removed and the magnitude of resistance of the piezoresistive device 110 increase.

On the other hand, the switching device 120 may be a device including one or more of other devices such as an ovonic threshold switch (OTS), a memristor, a Mott insulator, one or more transistors, resistors, and inverters.

Here, the circuit 100 for providing an artificial tactile neuron may quantify the pressure and the mechanical property of the external object based on an output voltage (Vout).

In this case, the output voltage (Vout) may be a difference between the input voltage and the voltage applied to the switching device 120.

Specifically, the circuit 100 for providing an artificial tactile neuron may quantify the pressure applied from the external object based on the frequency of the spike pattern of the output voltage.

Also, the circuit 100 for providing an artificial tactile neuron may quantify the mechanical property of the external object based on a change rate per unit time with respect to the frequency of the spike pattern of the output voltage.

In this case, the spike pattern of the output voltage refers to a potential change pattern shown in a repetitive form as illustrated in FIGS. 3 to 6*a*. Thereby, the spike pattern of the output voltage can replace an action potential function of the neuron.

The mechanical property may include one or more of stiffness, hardness and strength of the external object.

Meanwhile, the mechanical property has been described by exemplifying stiffness and hardness, but these are merely exemplary and are not necessarily limited thereto, and any physical quantity that is difficult to quantify may be included as the mechanical property of the present specification.

That is, the circuit 100 for providing an artificial tactile neuron may quantify an abstract physical quantity based on the output voltage.

Accordingly, the circuit 100 for providing an artificial tactile neuron can replace the somatic function of a sensory neuron that quantifies the pressure applied from the external object and the mechanical property of the external object.

Figure 2:
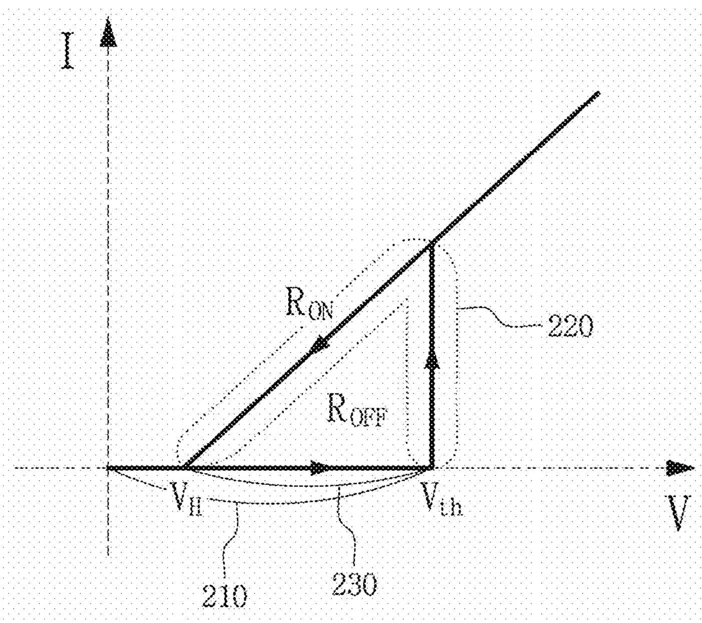
FIG. 2 is a graph showing current-voltage characteristics of the switching device of FIG. 1.

FIG. 2 is a graph illustrating current-voltage characteristics of the switching device 120 of FIG. 1.

Referring to FIG. 2, the switching device 120 has a different current-voltage relationship according to an on/off state of switching. Specifically, the switching device 120 maintains a switched-off state in a state in which no voltage is applied. However, when a voltage is applied to the switching device 120 and the applied voltage is less than a threshold voltage ($V_{th}$) (hereinafter, a first condition), there is a current-voltage relationship in which almost no current flows. In other words, the switching device 120 has a first curent-voltage relationship along a first path 210 under the first condition as shown in FIG. 2.

On the other hand, when a voltage is applied to the switching device 120 and the voltage applied to the switching device 120 reaches the threshold voltage ($V_{th}$) (hereinafter, a second condition), the resistance of the switching device 120 is rapidly lowered and the switching device 120 is switched on. This switched-on state is maintained until the voltage applied to the switching device 120 decreases and reaches the holding voltage ($V_H$). The switching device 120 has a second current-voltage relationship along a second path 220 under the second condition as shown in FIG. 2.

On the other hand, when the voltage applied to the switching device 120 in the switched-on state decreases to the holding voltage ($V_H$) (hereinafter, a third condition), the switching device 120 is in a switched-off state. As shown in FIG. 2, the switching device 120 has a third current-voltage relationship along a third path 230 under the third condition. In this case, the holding voltage ($V_H$) may be a value relatively smaller than the threshold voltage ($V_{th}$).

Correspondingly, the magnitude of resistance of the switching device 120 may change to an off-resistance value ($R_{OFF}$) in the switched-off state, and an on-resistance value ($R_{ON}$) in the switched-on state.

In this case, the off-resistance value ($R_{OFF}$) may be a value lower than the upper limit of the resistance range of the piezoresistive device 110 for the switched-off state. In other words, the resistance of the piezoresistive device 110 changes in inverse proportion to the applied pressure. In addition, when the applied pressure does not exist, the off-resistance value ($R_{OFF}$) may be a value less than the upper limit of the resistance range of the piezoresistive device 110 in order to maintain the switched-off state. The on-resistance value ($R_{ON}$) may be a relatively smaller value than the off-resistance value ($R_{OFF}$) for a reversible switched-on/off. For example, when the upper limit value of the resistance range of the piezoresistive device 110 is about 10 MΩ, the off-resistance value ($R_{OFF}$) of the switching device 120 is about 1 MΩ and the on-resistance value ($R_{ON}$) may be about 1 KΩ. Meanwhile, the resistance value of the piezoresistive device 110, the off resistance value ($R_{OFF}$) and the on-resistance value ($R_{ON}$) have been described as being 10 MΩ, 1 MΩ, and 1 MΩ, respectively, but this is exemplary and is not necessarily limited thereto.

Figure 3:
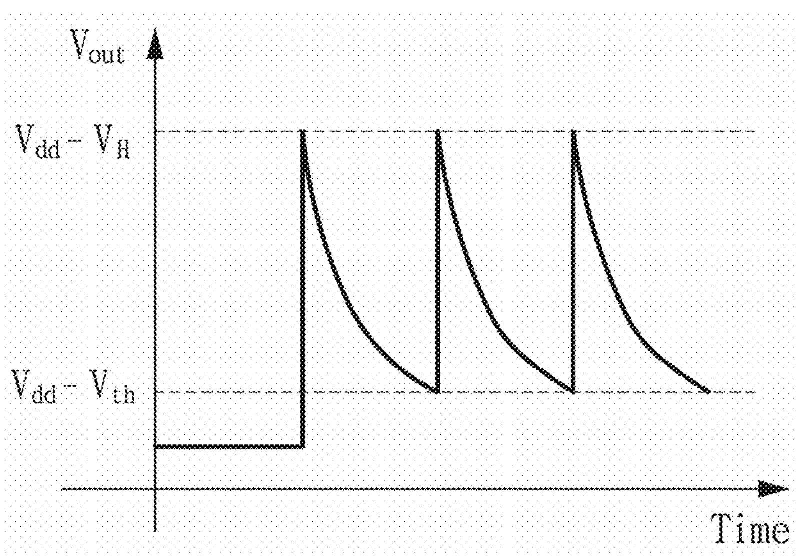
FIG. 3 is a graph illustrating an output voltage of a circuit for providing an artificial tactile neuron according to an embodiment.

FIG. 3 is a graph illustrating an output voltage of the circuit 100 for providing an artificial tactile neuron according to an exemplary embodiment.

As shown in FIG. 3, the circuit 100 for providing an artificial tactile neuron may encode the pressure applied from the external object into the spike pattern of the neuron based on the output voltage.

Here, the output voltage is a voltage drop generated in the piezoresistive device, and the voltage applied to the switching device 120 may be determined based on a voltage divider rule between the switching device 120 and the piezoresistive device 110.

For example, as shown in FIG. 1, when the piezoresistive device 110 and the switching device 120 are connected in series with an input power supply, the power supply voltage may be distributed in proportion to the resistance value of each component of the circuit.

However, the switching device 120 includes a parasitic capacitor component, and the parasitic capacitor is connected in parallel with a resistance component (a component having an on-resistance value and an off-resistance value according to an applied voltage). The capacitor component may dominate in the switched-off state, and the resistance component may dominate in the switched-on state. Accordingly, the speed at which the voltage is applied to the switching device 120 in the switched-off state is inversely proportional to the resistance value of the piezoresistive device 110 connected in series.

In this case, the magnitude of resistance of the piezoresistive device 110 is changed according to the magnitude of the pressure applied to the piezoresistive device 110, and the increase rate of the voltage applied to the switching device 120 depends on the magnitude of the pressure loaded by the external object. On the other hand, when the switching device 120 is in the switched-on state, the resistance component is dominant, so the applied voltage may be rapidly reduced.

Specifically, according to an embodiment, the process of calculating the output voltage of the circuit 100 for providing an artificial tactile neuron may be described as follows.

For the convenience of description, it is assumed that the switching device 120 is in the switched-off state, and the magnitude of resistance of the piezoresistive device 110 is inversely proportional to the applied pressure.

First, when the pressure applied to the piezoresistive device 110 from an external object increases, the magnitude of resistance of the piezoresistive device 110 decreases.

In this case, the voltage applied to the switching device 120 increases according to a voltage divider rule, and the increase rate is inversely proportional to the resistance of the piezoresistive device 110 connected in series.

Here, when the voltage applied to the switching device 120 reaches the threshold voltage ($V_{th}$), the switching device 120 performs a switched-on. In this case, the output voltage value becomes a value of $V_{dd}$-$V_{th}$.

In the switched-on state, the magnitude of resistance of the switching device 120 changes to an on-resistance value ($R_{ON}$), and the on-resistance value ($R_{ON}$) is smaller than the off-resistance value ($R_{OFF}$). The magnitude of the applied voltage of the switching device 120 decreases according to a voltage divider rule.

Here, when the voltage applied to the switching device 120 reaches the holding voltage ($V_H$), the switching device 120 performs a switch-off. In this case, the output voltage value becomes a value of $V_{dd}$-$V_H$.

In the switched-off state, the magnitude of resistance of the switching device 120 changes to the off-resistance value ($R_{OFF}$). Accordingly, since the capacitor component becomes dominant again in the switching device 120, the switch-on is performed when the voltage applied to the switching device 120 gradually increases again to reach the threshold voltage ($V_{th}$). In this case, the output voltage value becomes the value of $V_{dd}$-$V_{th}$ again. This switch-on/off forms one spike. This spike pattern is continuously generated as long as the input voltage and pressure of the appropriate magnitude are applied. In this case, the frequency of the spike is inversely proportional to the resistance value of the piezoresistive device 110, and is proportional to the magnitude of the applied pressure.

Similarly, according to another embodiment, the process of calculating the output voltage of the circuit 100 for providing an artificial tactile neuron may be described as follows.

For the convenience of description, it is assumed that the switching device 120 is in the switched-on state, and the magnitude of resistance of the piezoresistive device 110 is inversely proportional to the applied pressure.

First, when the pressure applied to the piezoresistive device 110 from an external object is removed, the magnitude of resistance of the piezoresistive device 110 increases.

In this case, the voltage applied to the switching device 120 decreases according to a voltage divider rule.

Here, when the voltage applied to the switching device 120 reaches the holding voltage ($V_H$), the switching device 120 performs the switch-off. In the switched-off state, the magnitude of resistance of the switching device 120 changes to the off-resistance value ($R_{OFF}$).

However, in a state in which the pressure is removed, the magnitude of resistance of the piezoresistive device 110 may be higher than the off-resistance value ($R_{OFF}$) of the switching device 120. Accordingly, the voltage applied to the switching device 120 is maintained in a state lower than the holding voltage, so that the switching device 120 may remain in the off-state.

Accordingly, the circuit 100 for providing an artificial tactile neuron according to an embodiment may have an event-driven characteristic in which a spike is generated only when pressure is applied, and no spike is generated in a state in which pressure is removed. Such event-based spike generation has the advantage of saving energy of a driving circuit.

Figure 4:
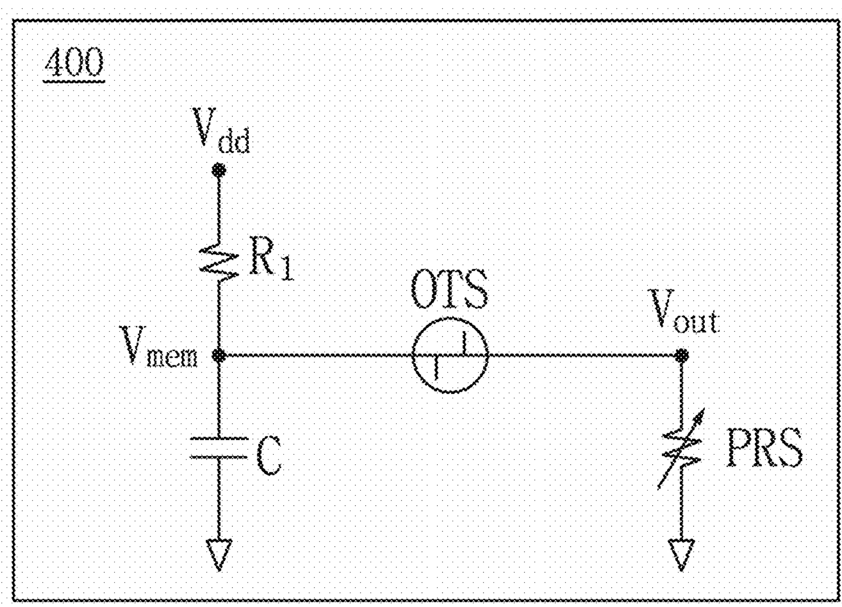
FIG. 4 is a circuit diagram illustrating a circuit for providing an artificial tactile neuron according to another embodiment.

FIG. 4 is a circuit diagram illustrating a circuit 400 for providing an artificial tactile neuron according to another embodiment.

Referring to FIG. 4, the circuit 400 for providing an artificial tactile neurons further includes an external capacitor.

According to an embodiment, the circuit 400 for providing an artificial tactile neuron may have a structure in which the switching device 120 is connected in series with the piezoresistive device 110, and the capacitor is connected in parallel with the serially connected switching device 120 and piezoresistive device 110.

Accordingly, the circuit 400 for providing an artificial tactile neuron may remove the lower limit of the resistance range of the piezoresistive device 110 by connecting the serially connected switching device 120 and piezoresistive device 110 and the capacitor in parallel. Accordingly, the piezoresistive device 110 has a technical advantage in that the range of the sensed pressure is widened.

In addition, the circuit 400 for providing an artificial tactile neurons enables additional control over the frequency range of the spike pattern of the output voltage by connecting the serially connected switching device 120 and piezoresistive device 110 and the capacitor in parallel. Meanwhile, in FIG. 4, the piezoresistive device 110 is illustrated as PRS and the switching device 120 is illustrated as OTS, but these are exemplary and the piezoresistive device 110 and the switching device 120 are not limited thereto.

Figure 5A:
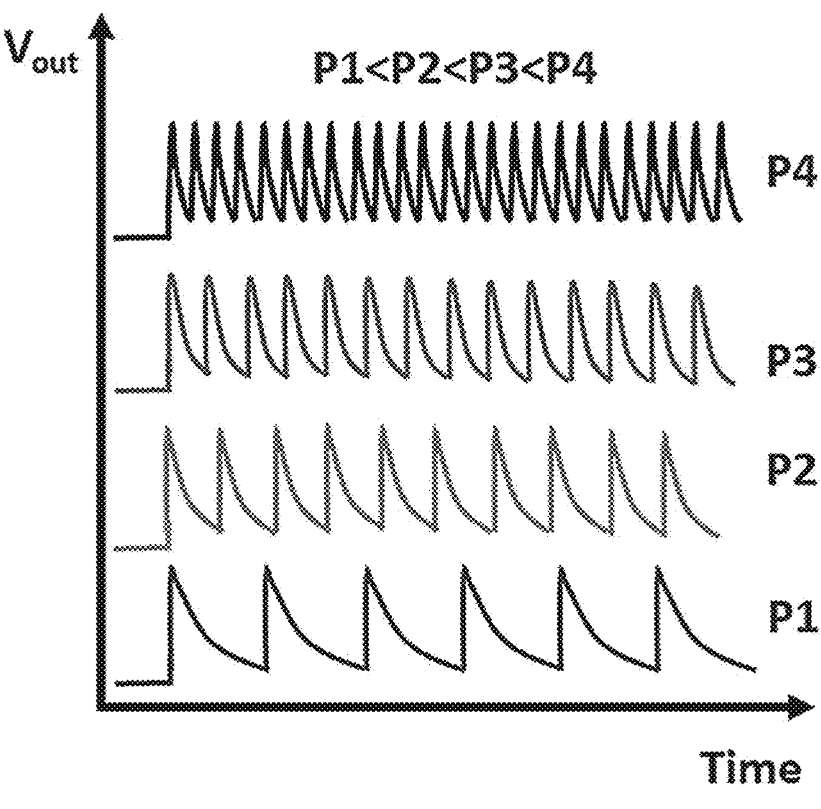
FIG. 5A is a graph illustrating an output voltage of a circuit for each pressure for providing an artificial tactile neuron according to an embodiment.

FIG. 5A is a graph illustrating an output voltage of the circuit 100 for each pressure for providing an artificial tactile neuron according to an embodiment.

P1, P2, P3, and P4 of FIG. 5A are independent variables expressing the magnitude of the pressure applied to the piezoresistive device 110 for each implementation cycle. For the convenience of description, it is assumed that there is a relationship of P4>P3>P2>P1.

Referring to FIG. 5A, the number of times the switching device 120 performs the switch-on/off is proportional to the amount of pressure applied to the piezoresistive device 110. That is, it can be confirmed that the frequency of the spike pattern of the output voltage of the circuit 100 for providing an artificial tactile neuron is proportional to the pressure applied to the piezoresistive device 110.

Figure 5B:
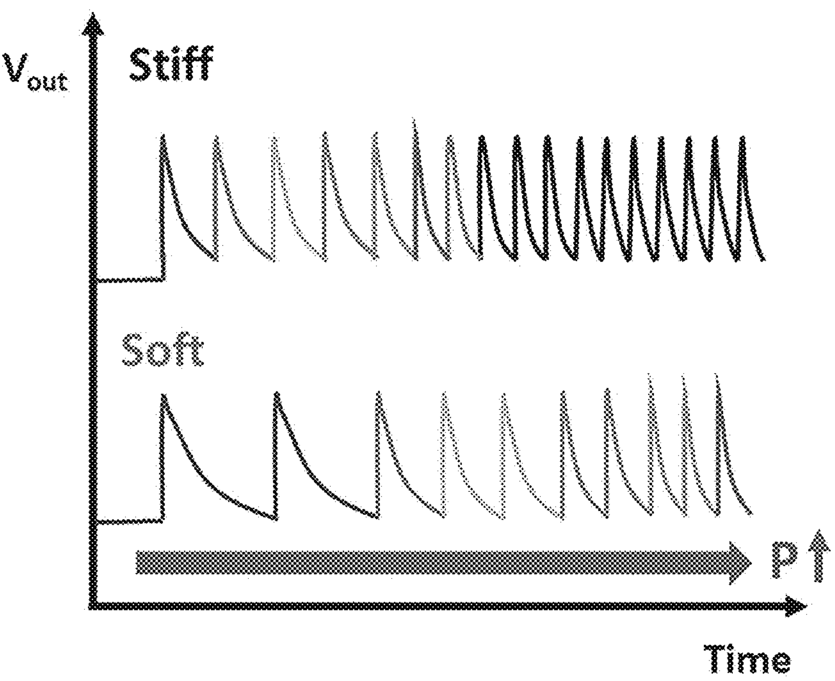
FIG. 5B is a graph illustrating an output voltage of a circuit for each stiffness for providing an artificial tactile neuron according to an embodiment.

FIG. 5B is a graph illustrating an output voltage of the circuit 100 for each stiffness for providing an artificial tactile neurons of FIG. 1.

For the convenience of description, it is assumed that a first material is a material stiffer than that of a second material, and correspondingly, the second material is a material softer than that of the first material. In addition, it is assumed that the magnitude of the pressure applied to the piezoresistive device 110 by each of the first material and the second material increases in proportion to time.

The graph disposed at the upper part of FIG. 5B is a graph illustrating the output voltage of the circuit for providing an artificial tactile neuron according to the pressure applied to the piezoresistive device 110 by the first material. The graph disposed at the bottom of FIG. 5B is a graph illustrating the output voltage of the artificial tactile neuron device according to the pressure applied to the piezoresistive device 110 by the second material.

Referring to FIG. 5B, when the same pressure is applied, the frequency change rate of the spike pattern for the first material is relatively higher than that for the second material.

The soft material undergoes the greatest deformation when pressure is applied, and thus, the soft material delays the propagation of force.

That is, it can be confirmed that a pressure change rate is in inverse proportion to the stiffness of the external object, and the pressure change rate per unit time for the external object is an index expressing the stiffness of the external object.

Accordingly, for the same pressure, the external object having a relatively low frequency change rate of the spike pattern per unit time may be indicated as a soft material, and the external object having a relatively high frequency change rate of the spike pattern per unit time may be indicated as a stiff material.

Figure 6A:
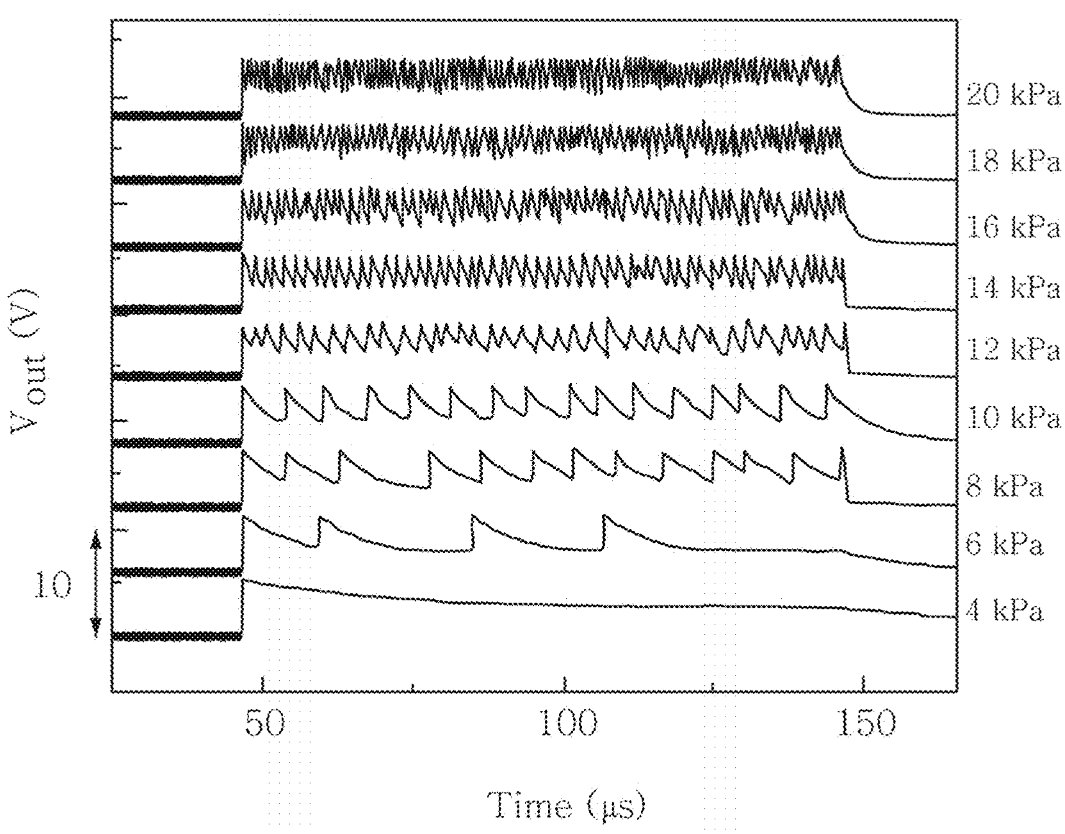
FIG. 6A is a graph illustrating an output voltage of a circuit for pressure in a small unit for providing an artificial tactile neuron according to an embodiment.

FIG. 6A is a graph illustrating an output voltage with respect to the pressure in a small unit of the circuit 100 for providing an artificial tactile neuron device of FIG. 1.

Referring to FIG. 6A, the circuit 100 for providing an artificial tactile neuron encodes the pressure in a small unit of 4 kPa to 20 kPa into a spike pattern based on an output voltage.

Figure 6B:
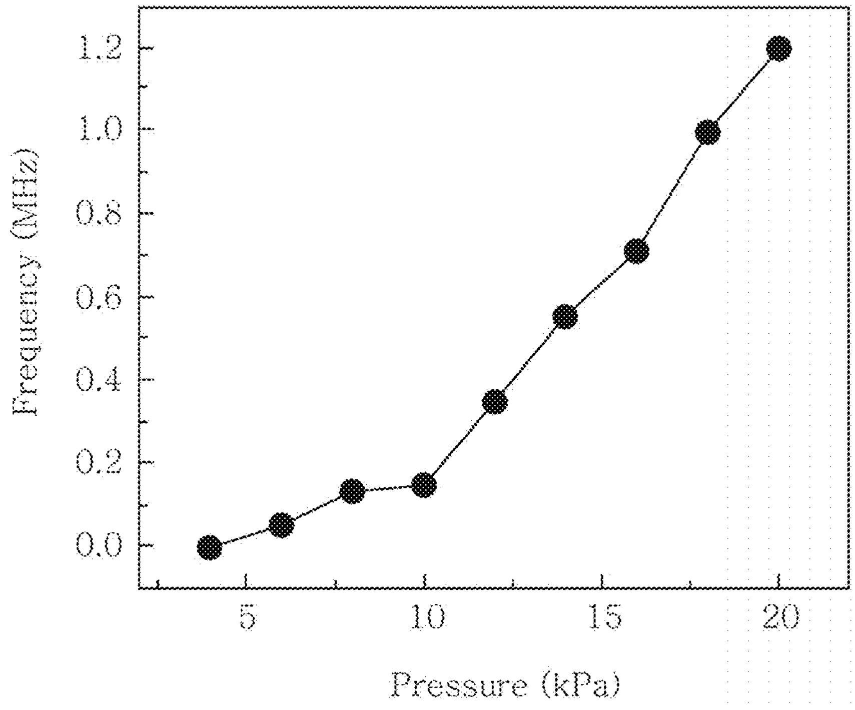
FIG. 6B is a graph illustrating a quantification result of the pressure of a circuit for providing an artificial tactile neuron according to an embodiment.

FIG. 6B is a graph illustrating an encoding result for the pressure in a small unit of the circuit 100 for providing an artificial tactile neuron of FIG. 1.

Referring to FIG. 6B, the circuit 100 for providing an artificial tactile neuron encodes the pressure in a small unit of 4 kPa to 20 kPa as a frequency of a spike pattern based on an output voltage.

Accordingly, the circuit 100 for providing an artificial tactile neuron may extend a measurement target to a soft material by using a high sensitivity characteristic, as well as a measurement range to the mechanical characteristic in a small unit.

Figure 7A:
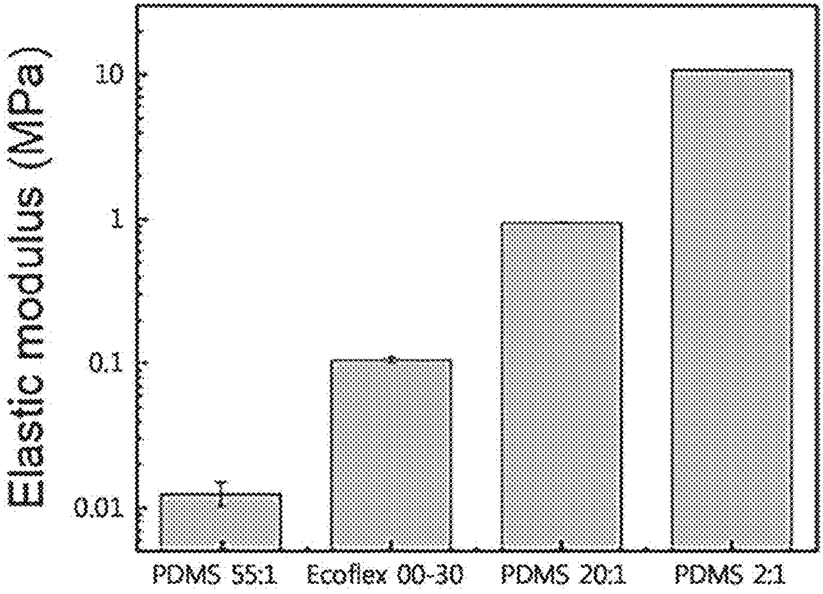
FIG. 7A is a graph illustrating the elastic moduli of external objects used to evaluate the performance of a circuit for providing an artificial tactile neuron according to an embodiment.

FIG. 7A is a graph illustrating an elastic moduli of an external object used in an experiment to evaluate the performance of the circuit 100 for providing an artificial tactile neuron according to an embodiment.

Specifically, the external objects used in the experiment are of a total of four types including PDMS 55:1, which is the softest material, PDMS 2:1, which is the stiffest material, Ecoflex 00-30 and PDMS 20:1, which are materials with stiffness in between.

In this case, the external object used in the experiment has an elastic modulus in the range of about 12.6 kPa to 10.7 MPa, and the range of elastic moduli used in the experiment is 12.6 kPa to 10.7 MPa.

Experimental results of the circuit 100 for providing an artificial tactile neuron according to an embodiment with respect to the above-described range will be described with reference to FIGS. 7B to 7D.

Figure 7B:
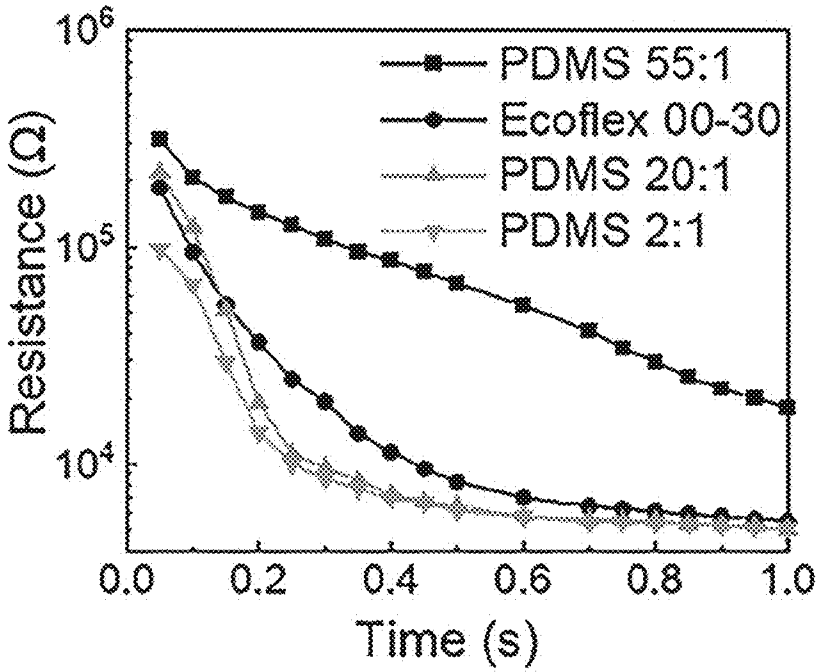
FIG. 7B is a graph illustrating the pressure applied from an external object having various elastic modulus of FIG. 7A as a resistance value of a piezoresistive device.

FIG. 7B is a graph illustrating the pressure applied from the external object having various elastic moduli of FIG. 7A as a resistance value of the piezoresistive device 110.

FIG. 7B shows the resistance value of the piezoresistive device 110 when pressure is applied to the piezoresistive device 110 from four types of external objects for 1 second at a level of 20 kPa.

At the onset of pressure, the softest material, PDMS 55:1, has the highest resistance value, and the stiffest material, PDMS 2:1, has the lowest resistance value.

Figure 7C:
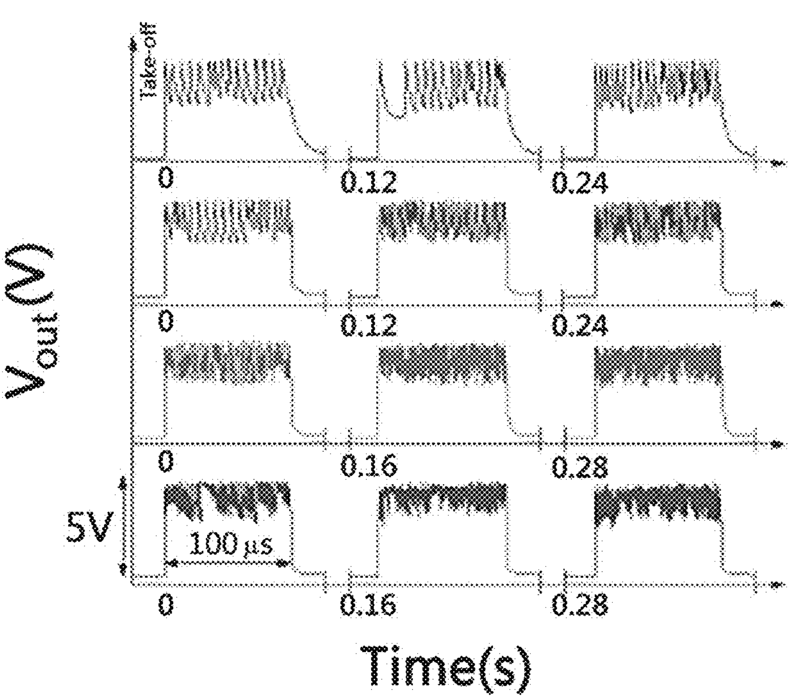
FIG. 7C is a graph in which the pressure applied from an external object having various elastic moduli of FIG. 7A is encoded as a spike pattern.

FIG. 7C is a graph in which the pressure applied from the external object having various elastic moduli of FIG. 7A is encoded as a spike pattern.

FIG. 7C illustrates the spike pattern encoded when pressure is applied to the piezoresistive device 110 from four types of external objects at a level of 20 kPa.

In FIG. 7C, the spike pattern from the top to the bottom corresponds to the order of PDMS 55:1, Ecoflex 00-30, PDMS 20:1, and PDMS 2:1, respectively, and it is found that the elastic modulus is proportional to the frequency of the spike pattern. On the other hand, in this case, the width of the voltage pulse is 100 us, and the period is 40 ms.

Figure 7D:
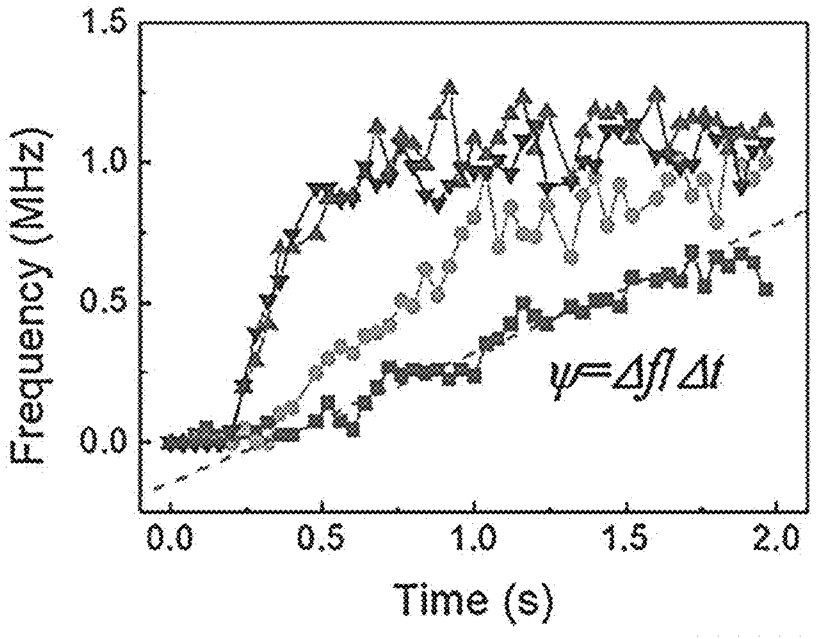
FIG. 7D is a graph illustrating a frequency change rate per unit time for an external object having various elastic modulus of FIG. 7A.

FIG. 7D is a graph illustrating a frequency change rate (φ) of a spike pattern per unit time for the external object having various elastic moduli of FIG. 7A.

Referring to FIG. 7D, the frequency of the spike pattern encoded by the circuit 100 for providing an artificial tactile neuron according to an embodiment changes more slowly with respect to time in a soft material than in a stiff material.

Specifically, the frequency change rate per unit time of the spike pattern for PDMS 55:1, which is the softest material, is 0.43 MHz, and the frequency change rate per unit time for the spike pattern for PDMS 2:1, which is the stiffest material, is 2.75 MHz. Accordingly, it can be confirmed that the frequency change rate per unit time of the spike pattern is proportional to the stiffness of the external object.

That is, the circuit 100 for providing an artificial tactile neuron according to an embodiment may identify the external object having a stiffness within the above-described range.

Furthermore, normal soft tissue has an elastic modulus in the range of several kPa to several tens of kPa, and tumors generally have a larger elastic modulus out of this range. Considering this, the circuit 100 for providing an artificial tactile neurons can easily distinguish between a normal soft tissue and an abnormal soft tissue.

Figure 8:
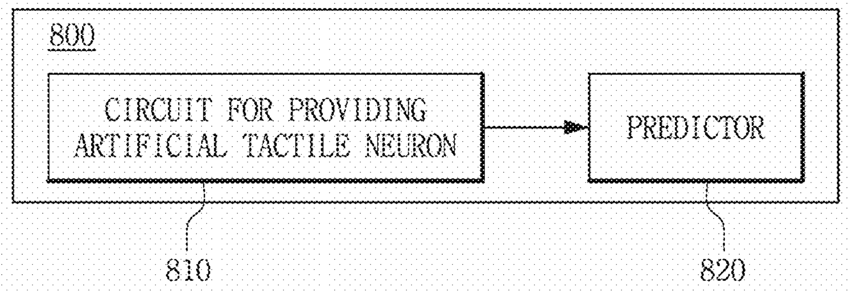
FIG. 8 is a block diagram illustrating an apparatus for predicting a disease based on an artificial tactile neuron according to an embodiment.

FIG. 8 is a block diagram illustrating an apparatus for predicting a disease based on an artificial tactile neuron 800 according to an embodiment.

Referring to FIG. 8, the apparatus 800 for predicting a disease based on an artificial tactile neuron according to an embodiment includes a circuit 810 for providing an artificial tactile neuron and a predictor 820.

According to an embodiment, the predictor 820 may be implemented using one or more physically separated devices, or may be implemented by one or more processors or a combination of one or more processors and software, and may not be clearly distinguished in specific operation, unlike the illustrated example.

In the example shown in FIG. 8, the circuit 810 for providing an artificial tactile neuron has the same configuration as that shown in FIG. 1, and thus a redundant description thereof will be omitted.

The predictor 820 predicts the disease of a diagnosis target by inputting the input data generated based on the quantified values for each of the pressure and mechanical property to a pretrained model.

In this case, the pretrained model may be an artificial neural network model trained to diagnose a disease with respect to a quantified value using a deep learning technique. The artificial neural network may include, for example, a Spiking Neuron Network (SNN) that mimics the biological operation structure of the brain, but is not necessarily limited to a specific artificial neural network structure.

In this case, the input data generated based on the quantified value may be, for example, an ultrasound elastography image generated based on an output value or a value including a time sequence for each pixel of the elastography image.

The accuracy test of a breast tumor ultrasound elastographic image classification of the apparatus for predicting a disease based on an artificial tactile neuron 800 according to an embodiment is evaluated as shown in Table 1 below.

TABLE 1

| Accuracy (%) | | Ground truth | |
|---|---|---|---|
| | | Benign | Malignant |
| Prediction | Benign | 87.04 ± 7.97 | 12.04 ± 4.14 |
| | Malignant | 12.96 ± 7.97 | 87.96 ± 4.14 |

That is, the apparatus for predicting a disease based on an artificial tactile neuron according to an embodiment may diagnose a disease with an average accuracy of 87.5% and a maximum accuracy of 95.8% with respect to disease diagnosis.

Although the above has been described with reference to the embodiments, it will be understood that those skilled in the art can variously modify and change the present invention within the scope without departing from the spirit and scope of the present invention described in the claims below.

DESCRIPTION OF REFERENCE NUMERALS

100: circuit for providing an artificial tactile neuron
400: circuit for providing an artificial tactile neuron
110: piezoresistive device
120: switching device
800: apparatus for predicting a disease based on an artificial tactile neuron
810: circuit for providing an artificial tactile neuron
820: predictor

What is claimed is:

1. A circuit for providing an artificial tactile neuron, comprising:
a piezoresistive device that receives pressure applied from an external object and changes a magnitude of resistance based on the pressure; and
a switching device that changes a magnitude of resistance based on a voltage applied from an input voltage,
wherein the pressure and a mechanical property of the external object are quantified from an output voltage set based on the input voltage and the voltage applied to the switching device,
wherein the switching device is in a switched-off state when no voltage is applied, performs a switched-on when the applied voltage reaches a threshold voltage or higher, performs the switched-off when the applied voltage reaches a holding voltage or less in the switched-on state, and performs the switched-on when the applied voltage again reaches the threshold voltage or higher.

2. The circuit for providing an artificial tactile neuron according to claim 1, wherein the pressure is quantified based on a frequency of a spike pattern of the output voltage, and the mechanical property of the external object is quantified based on a change rate per unit time of the frequency of the spike pattern.

3. The circuit for providing an artificial tactile neuron according to claim 1, wherein the mechanical property includes at least one of stiffness and hardness of the external object.

4. The circuit for providing an artificial tactile neuron according to claim 1, wherein the voltage applied to the switching device is applied based on a voltage divider rule between the switching device and the piezoresistive device.

5. The circuit for providing an artificial tactile neuron according to claim 1, wherein the magnitude of resistance of the switching device is changed to an off-resistance value in the switched-off state, and an on-resistance value smaller than the off-resistance value in the switched-on state.

6. The circuit for providing an artificial tactile neuron according to claim 5, wherein the switching device performs the switch-on when the applied voltage reaches the threshold voltage as the pressure applied to the piezoresistive device increases and the magnitude of resistance of the piezoresistive device decreases.

7. The circuit for providing an artificial tactile neuron according to claim 6, wherein the switching device performs the switch-off when the applied voltage reaches the holding voltage as the magnitude of resistance of the switching device decreases to the on-resistance value in the switched-on state.

8. The circuit for providing an artificial tactile neuron according to claim 7, wherein the switching device again performs the switch-on when the applied voltage reaches the threshold voltage as the magnitude of resistance of the switching device increases to the off-resistance value in the switched-off state.

9. The circuit for providing an artificial tactile neuron according to claim 1, wherein the switching device performs the switch-off when the applied voltage reaches the holding voltage as the pressure applied to the piezoresistive device is removed and the magnitude of resistance of the piezoresistive device increases.

10. The circuit for providing an artificial tactile neuron according to claim 5, wherein the magnitude of resistance of the switching device is changed to the on-resistance value when the magnitude of the applied voltage reaches the threshold voltage as the pressure applied to the piezoresistive device increases and the magnitude of resistance of the piezoresistive device decreases.

11. The circuit for providing an artificial tactile neuron according to claim 5, wherein the magnitude of resistance of the switching device is changed to the off-resistance value when the magnitude of the applied voltage reaches the holding voltage as the pressure applied to the piezoresistive device is removed and the magnitude of resistance of the piezoresistive device increases.

12. The circuit for providing an artificial tactile neuron according to claim 1, wherein the switching device is connected in series with the piezoresistive device, and the circuit further comprises a capacitor connected in parallel with the serially connected switching device and piezoresistive device.

13. The circuit for providing an artificial tactile neuron according to claim 1, wherein the switching device comprises an ovonic threshold switch (OTS).

14. The circuit for providing an artificial tactile neuron according to claim 1, wherein the circuit generates the spike pattern of the output voltage in an event-driven manner such that spikes are generated only when pressure is applied to the piezoresistive device and no spikes are generated when the pressure is removed.

15. An apparatus for predicting a disease based on an artificial tactile neuron, comprising:

a circuit for providing an artificial tactile neuron comprising a piezoresistive device that receives pressure applied to a diagnosis target and changes a magnitude of resistance based on the pressure, and a switching device that changes a magnitude of resistance based on a voltage applied from an input voltage, wherein the pressure and a mechanical property of the diagnosis target are quantified from an output voltage set based on the input voltage and the voltage applied to the switching device; and a predictor that predicts a disease of the diagnosis target by inputting input data generated based on a quantified value for each of the pressure and the mechanical property into a pretrained model.

16. The apparatus for predicting a disease based on an artificial tactile neuron according to claim 15, wherein the predictor comprises a spiking neural network (SNN).

* * * * *